(12) United States Patent
Hipperson

(10) Patent No.: US 8,597,263 B2
(45) Date of Patent: Dec. 3, 2013

(54) LOTION APPLICATION COMPARTMENT

(76) Inventor: Gerald Hipperson, Prague (CZ)

( * ) Notice: Subject to any disclaimer, the term of this patent is extended or adjusted under 35 U.S.C. 154(b) by 827 days.

(21) Appl. No.: 12/086,098

(22) PCT Filed: Dec. 4, 2006

(86) PCT No.: PCT/GB2006/004524
§ 371 (c)(1),
(2), (4) Date: Sep. 20, 2008

(87) PCT Pub. No.: WO2007/066084
PCT Pub. Date: Jun. 14, 2007

(65) Prior Publication Data
US 2010/0065655 A1  Mar. 18, 2010

(30) Foreign Application Priority Data
Dec. 5, 2005  (GB) .................................. 0524800.0

(51) Int. Cl.
*A61M 35/00* (2006.01)
(52) U.S. Cl.
USPC ........... 604/289; 604/540; 604/368; 604/389; 604/249; 604/295; 604/296; 454/49; 454/50; 454/51; 454/52; 454/53; 454/54; 454/55
(58) Field of Classification Search
USPC .................................. 604/249, 289, 295, 296
See application file for complete search history.

(56) References Cited

U.S. PATENT DOCUMENTS 3,483,572 A  12/1969 Hallum
3,868,950 A  3/1975 Kato (Continued)

FOREIGN PATENT DOCUMENTS

DE  2309411  8/1974
DE  93 19 158.8  4/1994

(Continued)

OTHER PUBLICATIONS

The American Heritage® Dictionary of the English Language, Fourth Edition copyright ©2000.*

*Primary Examiner* — Tatyana Zalukaeva
*Assistant Examiner* — Ilya Treyger
(74) *Attorney, Agent, or Firm* — MacMillan, Sobanski & Todd, LLC

(57) ABSTRACT

A lotion application compartment (10) includes an apparatus for topical application of a fluid to a human or animal body. The apparatus includes a spray nozzle (20) and a support (80) for the body. The apparatus further comprises of one or more of the following: a structure for moving the support, so as to change the distance between the body and the spray nozzle (20); a structure for varying the spray pattern, spray pressure, spray frequency and/or spray duty cycle of the nozzle (20); a structure for varying the rotational speed of the support (80); and a structure for raising the body's skin temperature directly by radiation. A lotion application compartment (10) consisting of apparatus for topical application of a fluid to a human or animal body, the apparatus comprising a spray nozzle (20) and a support (80) for the body. The apparatus further includes of one or more of the following: a structure for moving the support, so as to change the distance between the body and the spray nozzle (20); a structure for varying the spray pattern, spray pressure, spray frequency and/or spray duty cycle of the nozzle (20); a structure for varying the rotational speed of the support (80); and a structure for raising the body's skin temperature directly by radiation.

19 Claims, 3 Drawing Sheets

(56) References Cited

U.S. PATENT DOCUMENTS

| | | | |
|---|---|---|---|
| 4,469,951 | A | 9/1984 | Coco et al. |
| 4,856,520 | A | 8/1989 | Bilicki |
| 4,998,305 | A | 3/1991 | Davis |
| 5,073,996 | A | 12/1991 | Schinle |
| 5,205,490 | A | 4/1993 | Steinhardt et al. |
| 5,465,437 | A | 11/1995 | Herman |
| 5,664,593 | A | 9/1997 | McClain |
| 5,992,333 | A | 11/1999 | Lai |
| 6,117,118 | A | 9/2000 | Laughlin et al. |
| 6,199,557 | B1 | 3/2001 | Laughlin |
| 6,251,374 | B1 | 6/2001 | Laughlin |
| 6,298,862 | B1 | 10/2001 | Laughlin |
| 6,302,122 | B1 | 10/2001 | Parker et al. |
| 6,305,384 | B2 | 10/2001 | Laughlin |
| 6,322,554 | B1 | 11/2001 | Laughlin et al. |
| 6,325,783 | B1 | 12/2001 | Laughlin et al. |
| 6,352,861 | B1 * | 3/2002 | Copeland et al. ............ 436/46 |
| 6,374,434 | B1 | 4/2002 | Reid |
| 6,431,180 | B2 | 8/2002 | Laughlin |
| 6,439,243 | B2 | 8/2002 | Laughlin |
| 6,446,635 | B2 | 9/2002 | Laughlin |
| 6,468,508 | B1 | 10/2002 | Laughlin |
| 6,474,343 | B2 | 11/2002 | Laughlin |
| 6,656,455 | B2 | 12/2003 | Laughlin |
| 6,715,699 | B1 | 4/2004 | Greenberg et al. |
| 6,782,893 | B2 | 8/2004 | Laughlin |
| 7,378,055 | B2 * | 5/2008 | Lemme et al. ............ 422/64 |
| 2002/0005208 | A1 | 1/2002 | Laughlin |
| 2005/0022807 | A1 | 2/2005 | Laughlin |
| 2006/0037532 | A1 * | 2/2006 | Eidson ............ 118/31.5 |
| 2007/0107121 | A1 * | 5/2007 | Smith et al. ............ 4/615 |

FOREIGN PATENT DOCUMENTS

| | | | |
|---|---|---|---|
| EP | 1190694 | | 3/2002 |
| EP | 1247539 | | 10/2002 |
| EP | 1435209 | A1 * | 12/2002 |
| EP | 1270082 | | 1/2003 |
| EP | 1435209 | * | 6/2003 |
| EP | 1374937 | | 1/2004 |
| EP | 1435209 | | 7/2004 |
| GB | 2296656 | | 7/1996 |
| GB | 2410431 | | 8/2005 |
| WO | WO 00/54892 | | 9/2000 |
| WO | WO 00/62640 | | 10/2000 |
| WO | WO 03/082068 | * | 3/2002 |
| WO | WO 03/082068 | A2 * | 3/2002 |
| WO | WO 02/087700 | | 11/2002 |
| WO | WO 03/082068 | | 10/2003 |
| WO | WO03082068 | | 10/2003 |
| WO | WO 2004/091801 | | 10/2004 |
| WO | WO2004091801 | | 10/2004 |
| WO | WO 2005/094754 | | 10/2005 |

* cited by examiner

LOTION APPLICATION COMPARTMENT

CROSS-REFERENCE TO RELATED APPLICATIONS

This application is the National Phase of International Application PCT/GB2006/004524 filed Dec. 4, 2006 That International Application designated the U.S. and was published in English under PCT Article 21(2) on Jun. 14, 2007 as International Publication Number WO 2007/066084A1. PCT/GB2006/004524 claims priority to U.K. Application No. 0524800.0, filed Dec. 5, 2005. Thus, the subject nonprovisional application claims priority to U.K. Application No. 0524800.0, filed Dec. 5, 2005. The disclosures of both applications are incorporated herein by reference.

This invention relates to a lotion application compartment and particularly to a sunless tanning booth for delivering tanning lotion to the skin of a person using the booth.

BACKGROUND

In the sunless tanning industry it is known to use spray nozzles to apply a tanning lotion to the human body. Such systems are popular as they can provide an all year round tan without the problems associated with UV radiation. Typical arrangements consist of a booth with a plurality of fixed spray nozzles, which emit a fine mist of droplets. With these systems it is crucial that the skin is evenly coated to avoid a streaky or blotchy finish.

U.S. Pat. No. 5,664,593 is one of the earliest patents directed to spray booths, although it relates to the application of sun protection lotion. Disclosed is a chamber within which a fine mist is generated, however only the torso and limbs are enclosed. The spray is not focused on particular patches of the skin, and some of the lotion is therefore inevitably wasted. Furthermore, with this method an even coating is hard to achieve. This is acceptable for sun protection lotions as an even coating of the lotion is less crucial.

U.S. Pat. No. 5,922,333 presents a tanning booth where the person being coated is fully enclosed. To apply the tanning lotion all over, the person being coated rotates within the booth. However, it is difficult to control this particular system to ensure an even coating. In addition, lotion is wasted as not all of the lotion sprayed reaches the skin. Accordingly, apparatus must be provided to dispose of this excess lotion.

To obtain an even coating and minimise waste, it is suggested in WO0054892 to spray electrostatically charged droplets at an individual who is electrically grounded. However, such a device is unduly complicated and customers have expressed concerns for their safety.

Thus, with these problems in mind the present invention was conceived.

STATEMENT OF INVENTION

According to the present invention, there is provided an apparatus for topical application of a fluid to a human or animal body, the apparatus comprising a spray nozzle, a support for the body and means for moving the support, so as to change the distance between the body and the spray nozzle.

According to another aspect of the present invention, there is provided an apparatus for topical application of a fluid to a human or animal body, the apparatus comprising a spray nozzle, a support for the body and means for varying the spray pattern, spray pressure, spray frequency and/or spray duty cycle of the nozzle.

According to another aspect of the present invention, there is provided an apparatus for topical application of a fluid to a human or animal body, the apparatus comprising a spray nozzle, a support for the body and means for varying the rotational speed of the support.

According to another aspect of the present invention, there is provided an apparatus for topical application of a fluid to a human or animal body, the apparatus comprising a spray nozzle and means for raising the body's skin temperature directly by radiation.

The means to move the support may consist of a cam arrangement.

The means to move the support may consist of a crank arm assembly.

The means to move the support may consist of multiple axes of rotation.

The means to move the support may consist of a linear actuator.

The means for varying the rotational speed of the support may comprise an electric motor connected via a pulley arrangement.

The means for varying the rotational speed of the support may comprise an electric motor connected via a gear arrangement.

The apparatus may comprise means for synchronising the operation of the support and the spray nozzle.

The apparatus may comprise a high pressure pump which supplies the spray nozzle with fluid.

The means for varying the spray pattern, spray pressure, spray frequency and/or spray duty cycle of the nozzle may be provided via a valve, such as a solenoid valve.

The spray nozzle may be uniquely elevated and angled.

The apparatus may comprise a spray compartment.

The compartment may comprise an aluminium frame.

Glass panels may form walls of the compartment.

A base of the compartment may be formed from glass fibre reinforced plastic.

The support may have illuminated portions which mark a desired foot position on the support.

The apparatus may comprise short wave infrared lamps which heat the skin directly.

Glass panels and/or grills may protect the infrared lamps.

The apparatus may operate as a sauna.

A seat may be provided on the support.

The apparatus may comprise means for giving audio instructions to the user.

The apparatus may comprise means for washing out the compartment.

The apparatus may comprise means for heating the air, such as an electric heater.

The apparatus may comprise a handheld spray gun.

The fluid may be a sunless tanning lotion.

The apparatus may comprise a computer for controlling the apparatus.

A program running on the computer may adapt the operating parameters of the apparatus to a particular body shape.

The computer may provide means for synchronising the operation of the support and the spray nozzle.

The program may be specific to a particular individual.

The computer may communicate via a telephonic connection.

According to another aspect of the present invention, there is provided a method for topical application of a fluid to a human or animal body, with apparatus comprising a spray nozzle and a support for the body, wherein the rotational speed of the support is varied.

According to another aspect of the present invention, there is provided a method for topical application of a fluid to a human or animal body, with apparatus comprising a spray nozzle, wherein the body's skin temperature is raised directly by radiation.

According to another aspect of the present invention, there is provided a method for topical application of a fluid to a human or animal body, with apparatus comprising a spray nozzle and a support for the body, wherein the spray pattern, spray pressure, spray frequency and/or spray duty cycle of the nozzle are varied.

According to another aspect of the present invention, there is provided a method for topical application of a fluid to a human or animal body, with apparatus comprising a spray nozzle and a support for the body, wherein the support is moved, so as to change the distance between the body and the spray nozzle.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION OF PREFERRED EMBODIMENT

Applying an even coating of a substance to any body having a complex shape is difficult; but applying an even coating of lotion to a human body is further complicated by the enormous variation in shapes and sizes of the human population. This is particularly important in the application of sunless tanning lotions, as an even coating is required to avoid undesirable streaks and blotches.

Figure 1:
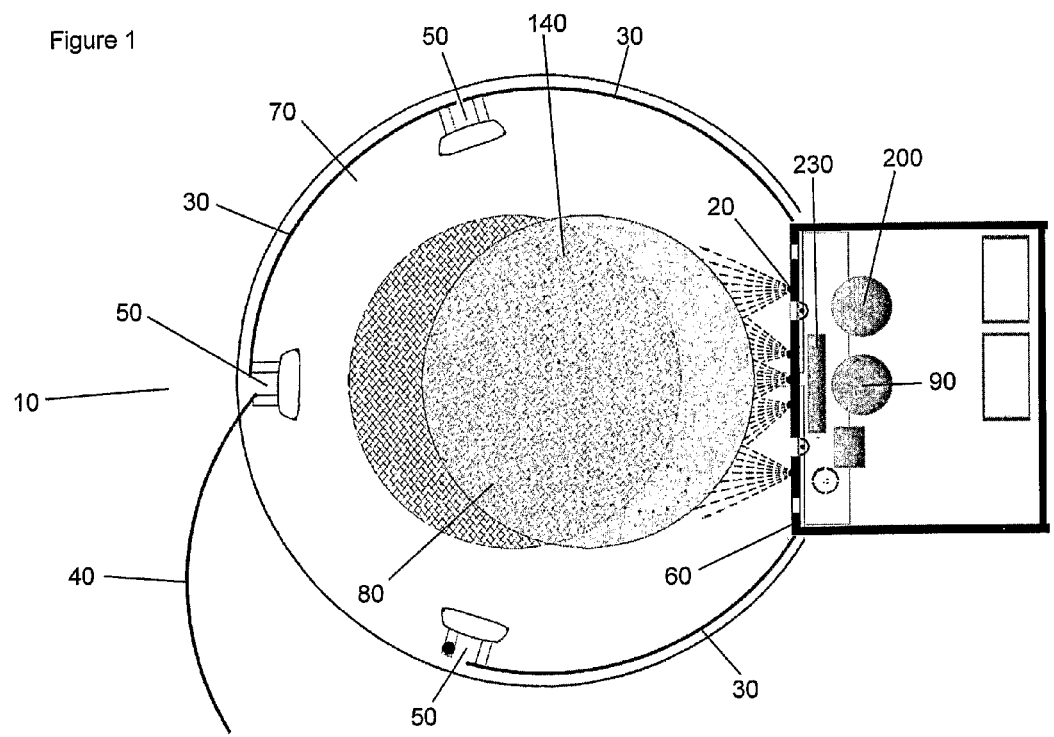
FIG. 1 is a plan view of a lotion application compartment.

With reference to FIG. 1, a lotion application compartment 10 comprises side-walls 30 and a door 40. The side-walls 30 and door 40 are supported by frame members 50. Preferably the side-walls 30 and door 40 are formed from glass and preferably the frame members 50 are made from aluminium. Alternatively, the side-walls 30 and/or door 40 could consist of a spray proof curtain. In the present embodiment the side-walls 30, door 40 and frame members 50 form a partial cylinder, which is fixed to a planar nozzle-wall 60. Although the present embodiment shows only one nozzle-wall 60, in alternative embodiments additional nozzle walls could be positioned around the perimeter of the compartment 10. The compartment 10 has a base 70 on which is supported a support 80. The base 70 and support 80 are preferably formed from glass reinforced plastic and polyethylene respectively. The support 80 has internally illuminated footprints 140 to mark the standing position. Preferably the compartment 10 has a diameter of approximately 140 cm and a height of approximately 225 cm.

Figure 2:
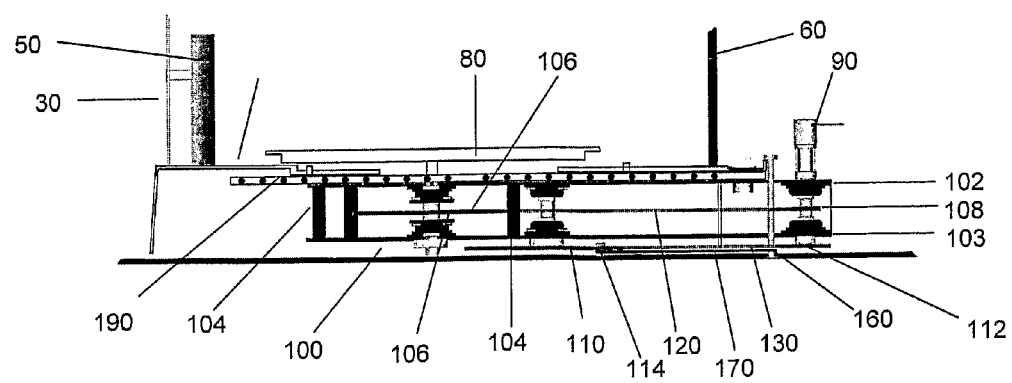
FIG. 2 is a side projection of the base of the lotion application compartment.

With reference to FIG. 2, the lotion application compartment 10 further comprises means for rotating the support 80. A support frame 100 is connected to an underside of the base 70. The support frame 100 comprises a pair of chassis plates 102,103 held apart by spacers 104. A support pulley 106, a first drive pulley 108, a second drive pulley 112 and a cam pulley 110 are rotatably mounted in bearings or bushes in the chassis plates 102, 103. A motor 90 is mounted on an end of the chassis plate 102, above the drive pulleys 108, 112 and drives the drive pulleys 108, 112 directly. In turn, the first drive pulley 108 drives the support pulley 106 to rotate via a belt or chain 120. Furthermore, the second drive pulley 112 drives the cam pulley 110 to rotate via a second belt or chain 130. The cam pulley 110 is connected to a crank arm 170, which is rotatably mounted at a first end to a floor anchor pin 160, which is fixed to the ground and at a second end to a radially outer edge of the cam pulley 110, which projects beneath the lower chassis plate 103. The second end of the crank arm 170 is situated beneath the cam pulley 110 and is rotatably connected to the cam pulley 110 by a pinned joint 114. The entire support frame 100, which includes the motor 90, the pulleys 106, 108, 110 and 112 and the support 80, is mounted on rollers 190 such that the support frame 100 is free to translate relative to the floor anchor pin 160.

Figure 3:
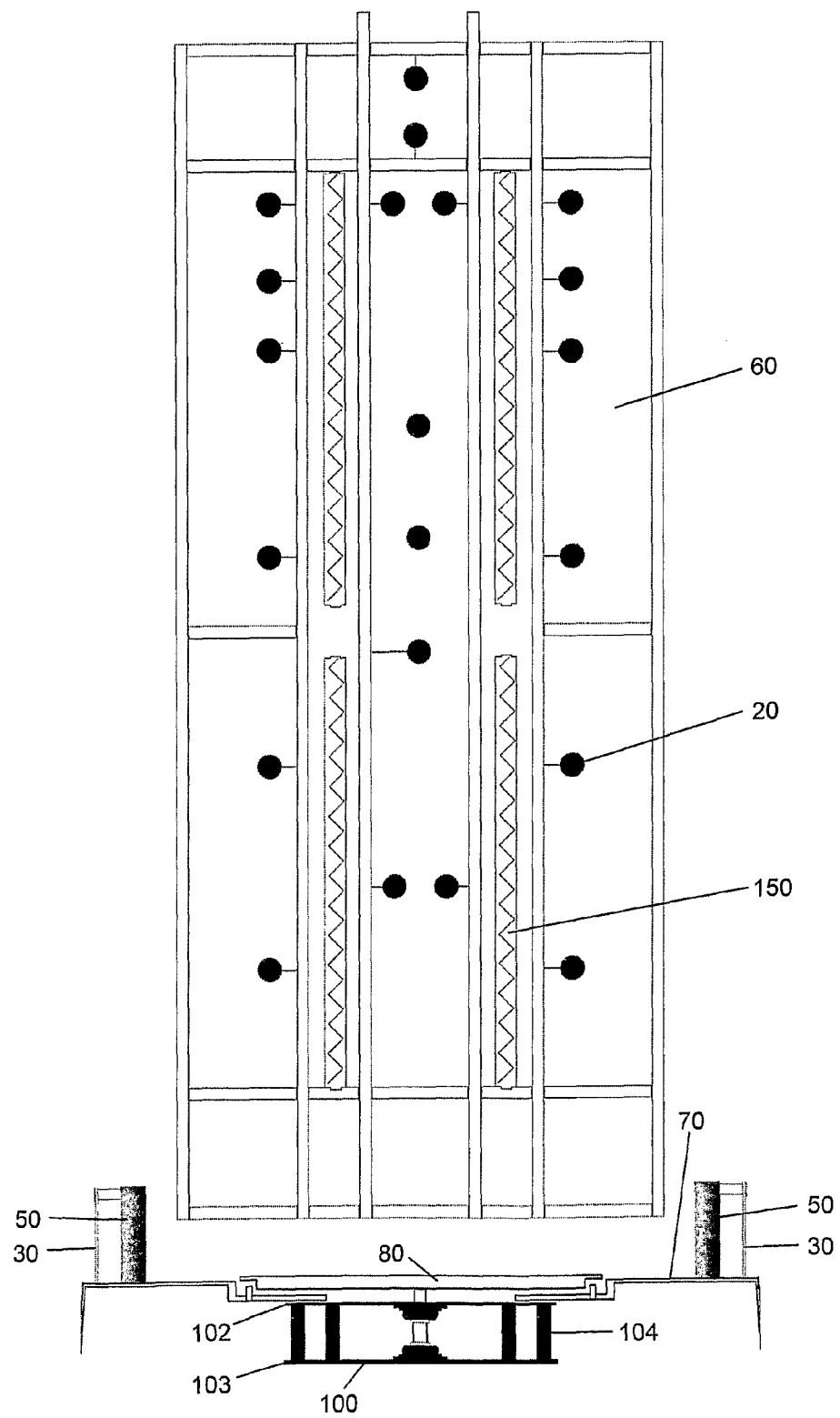
FIG. 3 is a side projection of the lotion application compartment of FIG. 1 showing the preferred nozzle arrangement.

With reference to FIG. 3, the lotion application compartment further comprises a plurality of spray nozzles 20 arranged in an array in the nozzle-wall 60, and fed with tanning fluid via a high pressure pump 200. Each nozzle 20 is uniquely angled and elevated. Also shown in FIG. 3 are heaters 150. These heaters 150 are preferably infrared lamps mounted in the nozzle-wall 60 and directed at the person being coated. The heaters 150 are preferably protected by ceramic glass and/or metal grills.

Figure 4:
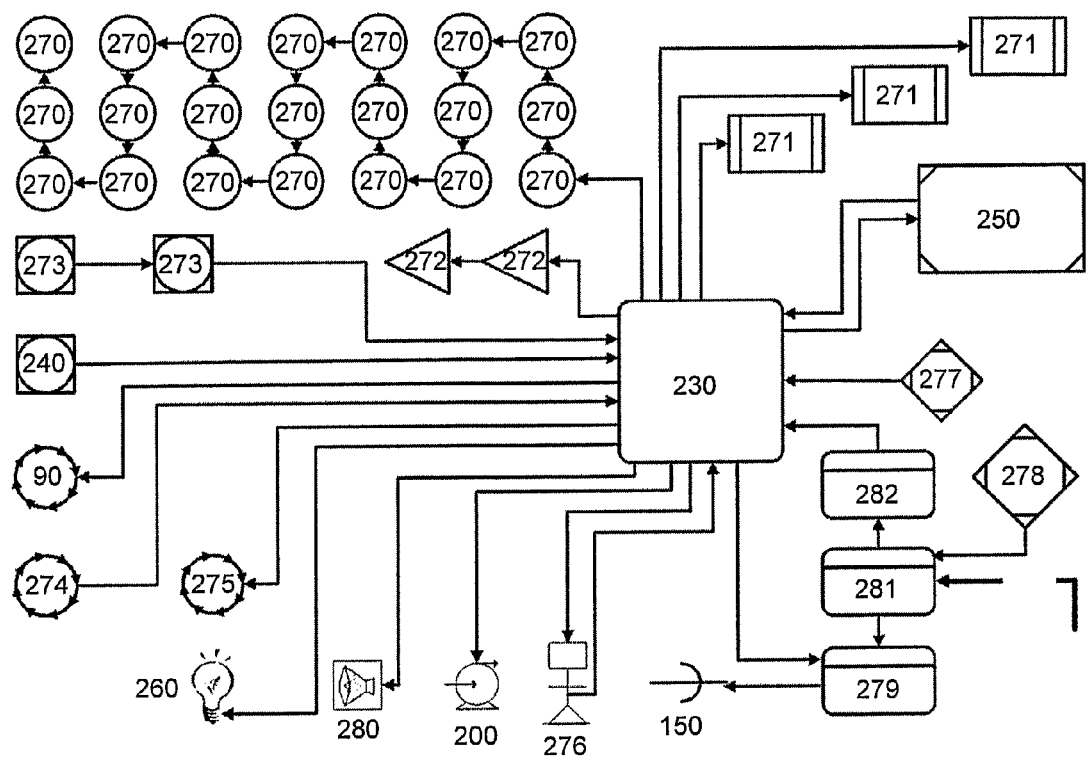
FIG. 4 is a schematic of a possible implementation for the control system.

With reference to FIG. 4 a computer processor 230, which controls various parameters, is provided. For example, the spray nozzle solenoid valves 220, motor 90, high pressure pump 200, door sensor 240, compartment light 260, speaker 270, pressure valves 271, water valves 272, level sensors 273, floor sensor 274, floor lights 275, data link 276, start button 277, emergency stop button 278, heater relay 279, power trip device 281, ACDC converter 282 and heaters 150 all interface with the computer processor 230. Furthermore, the computer processor 230 interfaces with the input control panel and output screen 250 for interaction with the user.

In operating, a person steps into the spray compartment and aligns their feet with footprints 140 on the support 80. The pump 200 is then operated to force tanning fluid from the nozzles 20 and the support 80 is driven to rotate, consequently, the person being coated does not to have to move or change position during the entire spraying process. The movement of the support 80 is synchronised to the spraying process to achieve an even distribution of the lotion and avoid unnecessary spraying of the lotion. Additionally, the movement of the support 80 and/or the spray parameters may be varied to make adjustments to the quantity of liquid each patch of skin receives, thereby affecting the final tan result. The support 80 preferably rotates at a speed of less than 6 rpm.

The position of the support 80 relative to the nozzles 20 can be varied by rotation of the cam pulley 110. As the cam pulley 110 is driven to rotate by the drive motor 90, the second end of the crank arm 170 rotates around the cam pulley 110, whilst the first end swings about the floor anchor pin 160. The entire support frame 100 is therefore forced to reciprocate backwards and forwards with the rotation of the cam pulley 110 (much like a piston in an internal combustion engine). By carefully selecting the drive ratios, the resulting motion can account for the topography of the human body and vary the distance of the body from the nozzle-wall 60 as appropriate to achieve even coverage of tanning lotion. In the preferred embodiment, a drive ratio of 2:1 between the cam pulley 110 and the support pulley 106 is desirable. The same effect could be achieved via a second rotating support with an eccentric axis or via a linear actuator. Note that the cam pulley 110 can be omitted from the arrangement in FIG. 2 or be disengaged from the drive motor to provide a simple rotation of the support 80 about a fixed axis.

The droplets leaving the spray nozzles 20 are of a size small enough to float gently and evenly on to the body yet large enough so that they do not remain airborne and attempt to leave the compartment 10. Typically the droplets are approximately 60 µm in diameter.

The nozzles 20 are uniquely angled and elevated to suit a particular body shape and are directed at specific patches of the human body. For each nozzle 20 the spray pressure, spray frequency and spray duty cycle are independently controlled via the solenoid valves 220 and this is done at each point during operation, which may be achieved to an accuracy of 1 ms. This therefore enables the spraying process to match the irregular shape of the human body and ensures that the various parts of the body are not under or over sprayed. Furthermore, it prevents spray from unnecessarily missing the body altogether, hence minimising waste.

The heaters 150 are located to pre-heat the skin of a person in the compartment. It is desirable that the skin is heated to greater than 38° C. prior to application of the lotion. The short wave infrared radiation penetrates deep into the skin into the subcutaneous layer below the epidermis and dermis layers and assists in opening of the skin's pores to aid absorption. Another important feature of this particular infrared frequency is that it only heats the person's skin and does not heat the air inside the cabin, thus making it a much more comfortable environment, preferably with a maximum temperature of +50° C.

The compartment 10 may also serve as a dry sauna. In this mode, the person is rotated at a slower speed to allow heat to penetrate all parts of the body. The compartment 10 could thus be used for muscle relaxation, the treatment of sports injuries or as a pre-exercise treatment minimising the body's warm-up time. In this mode a seat could be mounted on the support 80.

In addition to the infrared heaters 150, a number of air outlets could be used to direct pre-heated pressurised air through the nozzle-wall 60 of the compartment 10 on to the person's skin to aid drying of the skin after application. After each session an automatic compartment washing cycle starts. Just a few liters of water sprayed at high pressure are required to clean all the surfaces the last user of the compartment may have made contact with.

Uniquely, a plurality of software programs, cater for different body shapes and sizes and the computer processor 230 uses these software programs. Each program controls when each nozzle 20 is operated. For example, for a particular nozzle 20 of the preferred embodiment, 320 bursts of lotion could be emitted in one of 17,900 possible time slots during the process. Furthermore, the software programs also vary the position, speed and direction of the rotating support 80 and the location of its axis of rotation. The software program carefully synchronises the support position with the spray parameters to ensure an even coating of the lotion.

A previously-proposed handheld spray gun, which may be controlled by the software program, can be incorporated into the compartment so that those preferring this style of personal spraying have it available.

The software may control audio instructions synchronised to the process, advising and informing the customer about the process via the speaker 280. A specific language can be selected for these messages.

The software in the system can be controlled or updated telephonically via an integrally installed data link 276. This link allows downloading of software and also offers an up-link to remotely monitor the serviceability of the system from anywhere in the world. Furthermore, the activity of the system, for example, how many times the system is used, on which day, at what time, which tanning program was used and how much tanning lotion the salon operator has in stock could all be obtained.

The compartment 10 has several safeguards monitoring the system regarding spray pressures, liquid quantities and support rotation synchronisation. These automatically prevent the system starting the process if it is going to be unable to complete it correctly or safely.

This compartment 10 could be used for the treatment of skin diseases or other conditions, the decontamination of skin, or for cosmetic treatment. A variety of substances could be applied, for example, these include, but are not limited to, sunless tanning products based on DHA, dihydroxyacetone or otherwise, insect repellents, sunscreens, burn treatment agents, skin toners and moisturisers, skin bleaches and/or artificial colourings, body hair bleaching products, body hair removal products and nutriments or vitamins.

The invention claimed is:

1. An apparatus that is adapted to apply a fluid to a human or animal body comprising:
   a spray nozzle that is adapted allow a fluid to flow therethrough;
   a support that is movable relative to the spray nozzle and that is adapted to support a human or animal body thereon; and
   a processor programmed to operate the spray nozzle in synchronization with the movement of the support such that the parameters of fluid flow through the spray nozzle are varied in response to the position of the support relative to the spray nozzle.

2. The apparatus defined in claim 1 further including a pump that supplies the fluid through a valve to the spray nozzle, and wherein the processor operates the valve in synchronization with the movement of the support such that the flow of fluid through the spray nozzle is varied in response to the position of the support relative to the spray nozzle.

3. The apparatus defined in claim 1 wherein the processor varies one of a spray pattern, a spray pressure, a spray frequency, or a spray duty cycle of the spray nozzle.

4. The apparatus defined in claim 1 wherein the processor causes the flow of fluid through the spray nozzle to be applied in a plurality of timed bursts.

5. The apparatus defined in claim 1 wherein the support is rotatable relative to the spray nozzle.

6. The apparatus defined in claim 1 wherein the support reciprocates relative to the spray nozzle.

7. The apparatus defined in claim 1 wherein the support is both rotatable and reciprocates relative to the spray nozzle.

8. The apparatus defined in claim 1 wherein the support is movable relative to the spray nozzle at varying speeds.

9. The apparatus defined in claim 1 wherein the support is moved by a cam arrangement.

10. The apparatus defined in claim 1 wherein the support is moved by a crank arm assembly.

11. The apparatus defined in claim 1 wherein the support is moved by a linear actuator.

12. The apparatus defined in claim 1 wherein the support is moved by an electric motor connected to the support by a pulley arrangement.

13. The apparatus defined in claim 1 wherein the support is moved by an electric motor connected to the support by a gear arrangement.

14. The apparatus defined in claim 1 further including a heater that is adapted to pre-heat the human or animal body on the support.

15. An apparatus that is adapted to apply a fluid to a human or animal body comprising:
   a spray nozzle that is adapted allow a fluid to flow therethrough;
   a support that is movable relative to the spray nozzle and that is adapted to support a human or animal body thereon; and
   a processor programmed to operate the spray nozzle in synchronization with the movement of the support such that the parameters of fluid flow through the spray nozzle are varied in response to the position of the support relative to the spray nozzle, wherein the support is either:
   (a) both rotatable and reciprocates relative to the spray nozzle;
   (b) moved by a cam arrangement;
   (c) moved by a crank arm assembly; or
   (d) moved by a linear actuator.

16. The apparatus defined in claim 15 wherein the support is both rotatable and reciprocates relative to the spray nozzle.

17. The apparatus defined in claim 15 wherein the support is moved by a cam arrangement.

18. The apparatus defined in claim 15 wherein the support is moved by a crank arm assembly.

19. The apparatus defined in claim 15 wherein the support is moved by a linear actuator.

\* \* \* \* \*